(12) United States Patent
Faram

(10) Patent No.: US 10,576,221 B2
(45) Date of Patent: Mar. 3, 2020

(54) INTERNAL NEBULIZER SEAL AND METHOD OF USE

(71) Applicant: Joseph Dee Faram, Dallas, TX (US)

(72) Inventor: Joseph Dee Faram, Dallas, TX (US)

(73) Assignee: Caddo Medical Technologies LLC, Dallas, TX (US)

( * ) Notice: Subject to any disclaimer, the term of this patent is extended or adjusted under 35 U.S.C. 154(b) by 0 days.

(21) Appl. No.: 16/422,652

(22) Filed: May 24, 2019

(65) Prior Publication Data
US 2019/0314584 A1 Oct. 17, 2019

Related U.S. Application Data

(62) Division of application No. 15/934,519, filed on Mar. 23, 2018, now Pat. No. 10,342,935.
(Continued)

(51) Int. Cl.
*A61M 11/00* (2006.01)
*A61M 11/02* (2006.01)
(Continued)

(52) U.S. Cl.
CPC ............ *A61M 11/02* (2013.01); *A61M 11/06* (2013.01); *A61M 15/004* (2014.02); *A61M 15/0013* (2014.02); *A61M 15/0016* (2014.02); *A61M 15/0038* (2014.02); *A61M 15/0091* (2013.01); *A61M 15/0095* (2014.02); *A61M 16/0833* (2014.02); *A61M 16/0866* (2014.02); *A61M 16/208* (2013.01); *A61M 11/002* (2014.02); *A61M 11/04* (2013.01); *A61M 11/08* (2013.01); *A61M 15/002* (2014.02); *A61M 15/009* (2013.01); *A61M 15/0021* (2014.02);
(Continued)

(58) Field of Classification Search
CPC ...... A61M 11/02; A61M 11/04; A61M 11/06; A61M 11/08
See application file for complete search history.

(56) References Cited

U.S. PATENT DOCUMENTS 2,726,896 A 12/1955 McKinnon
3,172,406 A 3/1965 Bird et al.
(Continued)

FOREIGN PATENT DOCUMENTS

EP 1417982 A2 5/2004
GB 2055307 A 3/1981
(Continued)

OTHER PUBLICATIONS

Robert M. Kacmarek, Humidity and Aerosol Therapy, Foundations of Respiratory Care, 1992, pp. 793-824, Churchill Livingstone Inc., New York, United States.
(Continued)

*Primary Examiner* — Bradley H Philips
(74) *Attorney, Agent, or Firm* — Hitchcock Evert LLP

(57) ABSTRACT

The invention relates to an internal seal system. The internal seal may be incorporated into a pre-filled, small-volume nebulizer assembly with a T-connector. The small-volume nebulizer may be pre-filled with at least one unit-dose of medicine and hermetically sealed until use by an input port seal and the internal seal. The internal seal may operate as a valve when the assembly is changed into a second configuration.

4 Claims, 6 Drawing Sheets

Related U.S. Application Data

(60) Provisional application No. 62/589,360, filed on Nov. 21, 2017.

(51) Int. Cl.

| | |
|---|---|
| *A61M 15/00* | (2006.01) |
| *A61M 16/20* | (2006.01) |
| *A61M 16/08* | (2006.01) |
| *A61M 11/06* | (2006.01) |
| *A63B 23/18* | (2006.01) |
| *A61M 16/14* | (2006.01) |
| *A61M 11/04* | (2006.01) |
| *A61M 11/08* | (2006.01) |

(52) U.S. Cl.
CPC ......... *A61M 15/0028* (2013.01); *A61M 16/14* (2013.01); *A63B 23/18* (2013.01)

(56) References Cited

U.S. PATENT DOCUMENTS

| | | |
|---|---|---|
| 3,762,409 A | 10/1973 | Lester |
| 3,774,602 A | 11/1973 | Edwards |
| 3,945,378 A | 3/1976 | Paluch |
| 4,036,919 A * | 7/1977 | Komendowski ...... A61M 16/16 261/122.1 |
| 4,150,071 A | 4/1979 | Pecina |
| 4,253,468 A | 3/1981 | Lehmbeck |
| 4,261,354 A | 4/1981 | Nelson |
| 4,367,182 A * | 1/1983 | Kienholz .............. A61M 16/16 261/122.1 |
| 4,534,343 A | 8/1985 | Nowacki et al. |
| 4,595,002 A | 6/1986 | Michaels et al. |
| 4,657,007 A | 4/1987 | Carlin et al. |
| 4,951,661 A | 8/1990 | Sladek |
| 5,012,804 A | 5/1991 | Foley et al. |
| 5,027,809 A | 7/1991 | Robinson |
| 5,337,962 A | 8/1994 | Erb et al. |
| 5,357,945 A | 10/1994 | Messina |
| 5,364,615 A | 11/1994 | Debs et al. |
| 5,429,122 A | 7/1995 | Zanen et al. |
| 5,490,630 A | 2/1996 | Hecker |
| 5,579,757 A | 12/1996 | McMahon et al. |
| 5,584,285 A | 12/1996 | Salter et al. |
| 5,727,542 A | 3/1998 | King |
| 5,813,401 A | 9/1998 | Radcliff et al. |
| 5,823,179 A | 10/1998 | Grychowski et al. |
| 5,826,570 A | 10/1998 | Goodman et al. |
| 5,864,097 A | 1/1999 | Alvino |
| 6,044,841 A | 4/2000 | Verdun et al. |
| 6,257,231 B1 | 7/2001 | Shick et al. |
| 6,355,002 B1 | 3/2002 | Faram et al. |
| 6,363,932 B1 | 4/2002 | Forchione et al. |
| 6,390,090 B1 | 5/2002 | Piper |
| 6,412,481 B1 | 7/2002 | Bienvenu et al. |
| 6,422,234 B1 | 7/2002 | Bacon |
| 6,510,846 B1 | 1/2003 | O'Rourke |
| 6,632,842 B2 | 10/2003 | Chaundry et al. |
| 6,663,574 B2 | 12/2003 | Faram et al. |
| 6,679,250 B2 | 1/2004 | Walker et al. |
| 6,722,364 B2 | 4/2004 | Connelly et al. |
| 6,923,175 B2 | 8/2005 | Poole et al. |
| 6,994,083 B2 | 2/2006 | Foley et al. |
| 7,191,780 B2 | 3/2007 | Faram |
| 7,267,120 B2 | 9/2007 | Rustad et al. |
| 7,802,568 B2 | 9/2010 | Eicher et al. |
| 7,909,033 B2 | 3/2011 | Faram |
| 8,051,854 B2 | 11/2011 | Faram |
| 8,539,951 B1 | 9/2013 | Meyer et al. |
| 9,050,434 B2 | 6/2015 | Faram |
| 9,151,425 B2 | 10/2015 | Faram |
| 9,566,397 B2 | 2/2017 | Faram |
| 9,849,254 B2 | 12/2017 | Faram |
| 2001/0022279 A1 | 9/2001 | Denyer et al. |
| 2002/0162554 A1 | 11/2002 | Loescher |
| 2004/0031485 A1 | 2/2004 | Rustad et al. |
| 2005/0217666 A1 | 10/2005 | Fink et al. |
| 2006/0021613 A1 | 2/2006 | Overlander |
| 2007/0119449 A1 | 5/2007 | Boehm et al. |
| 2008/0078383 A1 | 4/2008 | Richards et al. |
| 2009/0050141 A1 | 2/2009 | King et al. |
| 2009/0188500 A1 | 7/2009 | Faram |
| 2009/0272820 A1 | 11/2009 | Foley et al. |
| 2010/0095958 A1 | 4/2010 | King et al. |
| 2011/0100360 A1 | 5/2011 | Faram |
| 2011/0209700 A1 | 9/2011 | Kreutzmann et al. |
| 2014/0048062 A1* | 2/2014 | Faram ................... A61M 11/00 128/200.18 |
| 2018/0071464 A1 | 3/2018 | Faram |
| 2019/0151572 A1 | 5/2019 | Faram |

FOREIGN PATENT DOCUMENTS

| | | |
|---|---|---|
| JP | 08-508671 A | 9/1996 |
| JP | 2004-535845 A | 12/2004 |
| JP | 2005-520641 A | 7/2005 |
| JP | 56-66345 U | 2/2015 |
| WO | 199520989 A1 | 8/1995 |
| WO | 2002055142 A2 | 7/2002 |
| WO | 2003080149 A2 | 10/2003 |
| WO | 2006006963 A2 | 1/2006 |
| WO | 2008144358 A1 | 11/2008 |
| WO | 2011080761 A1 | 7/2011 |
| WO | 2019103957 A1 | 5/2019 |

OTHER PUBLICATIONS

Colin Reisner, Joseph Lee, Arthur Kotch, and Gregory Dworkin, Comparison of Volume Output from Two Different Continuous Nebulizer Systems, Annals of Allergy, Asthma & Immunology, Feb. 1996, pp. 209-213, vol. 76.

Harriet Meyer, Antibacterial Agent in Some Asthma Medications Linked to Airway Constriction, UF Scientists Find, UF News, Jan. 11, 2001, pp. 1-2.

James B. Fink and Rajiv Dhand, Aerosol Therapy, Respiratory Care Clinics of North America, Jun. 2001, pp. 131-340, vol. 7, No. 2, W.B. Saunders Company, A Harcourt Health Sciences Company, Philadelphia, United States.

James B. Fink and Bruce K. Rubin, Aerosol Therapy for Children, Respiratory Care Clinics of North America Aerosol Therapy, Jun. 2001, pp. 175-213, vol. 7, No. 2, W.B. Saunders Company, A Harcourt Health Sciences Company, Philadelphia, United States (article from FINK book above).

U.S. Department of Health and Human Services, Food and Drug Administration, Center for Drug Evaluation and Research (CDER), Center for Biologics Evaluation and Research (CBER), Container Closure Systems for Packaging Human Drugs and Biologics Questions and Answers, Guidance for Industry, May 2002, pp. 1-6, United States.

Julie Applyby, I Will Breathe Easier: Safety Concerns Grow Over Pharmacy-Mixed Drugs, 2005, pp. 1-5, USA Today, United States.

Matthew Grissinger, Errors in the Making: Nearly Unreadable Labeling of Plastic Ampules for Nebulizing Agents, Medication Errors, P&T Journal, May 2005, vol. 30, No. 5, pp. 255-258.

Jamalvi SW, Raza SJ, Naz F, Shamim S, and Jamalvi SM, Management of Acute Asthma in Children Using Metered Dose Inhaler and Small Volume Nebulizer, J Pak Med Association, Dec. 2006, 1 page, PubMed.

Chatburn RL and McPeck M., A New System for Understanding Nebulizer Performance, Respir Care, Aug. 2007, 1 page, PubMed.

Catherine A. O'Malley et al., A Day in the Life of a Nebulizer: Surveillance for Bacterial Growth in Nebulizer Equipment of Children With Cystic Fibrosis in the Hospital Setting, Respiratory Care, Mar. 2007, pp. 258-262, vol. 52, No. 3.

Hoisington ER, Chatburn RL, and Stoller JK, A Comparison of Respiratory Care Workload with 2 Different Nebulizers, Respir Care, Apr. 2009, 1 page, PubMed.

(56) References Cited

OTHER PUBLICATIONS

Official Action issued for Japanese Patent Application No. 2010-508563, Mailing No. 80146, dated Feb. 20, 2015, 6 pages (translation included).

* cited by examiner

INTERNAL NEBULIZER SEAL AND METHOD OF USE

CROSS-REFERENCE TO RELATED APPLICATION

This application is a divisional of U.S. patent application Ser. No. 15/934,519 filed on Mar. 23, 2018, which claims the benefit of priority from U.S. Provisional Patent Application No. 62/589,360 filed on Nov. 21, 2017, both of which are incorporated herein by reference.

FIELD OF THE DISCLOSURE

The invention relates generally to the field of seals.

BACKGROUND

Seals are used in various applications. For example, U.S. patent application Ser. No. 11/748,907 filed on May 15, 2007, discloses a pre-filled, small-volume nebulizer with caps sealing the input and output of the small-volume nebulizer. U.S. Pat. No. 9,566,397—a continuation-in-part application from the '907 application—issued Feb. 14, 2017, discloses a small-volume nebulizer with a T component with three seals to prevent contamination prior to use. The '397 patent also discloses a one-way valve in the T component that facilitates airflow from a nebulizer to a patient during inhalation and seals the nebulizer output to stop airflow from the nebulizer during exhalation. The '907 application and '397 patent are incorporated herein by reference.

SUMMARY

The present disclosure teaches an apparatus with an internal sealing and opening system.

Some embodiments of the present disclosure provide an apparatus with a pre-filled, small-volume nebulizer combined with a T component and include an internal seal in the output of the nebulizer. The pre-filled, small-volume nebulizer may include a siphon, a jet and a baffle within a housing. A unit-dose of medication may be also contained within the housing by an input port seal and the internal seal in the output of the nebulizer. In some embodiments, the nebulizer includes external threads for connecting to the T component.

The T component includes a horizontal tube (or patient interface tube) having two ends and a vertical tube. The horizontal tube may have a first port with a mouthpiece and a second port with a flow restrictor in some embodiments. The first port may alternatively be operable to connect to a patient interface component, such as a mouthpiece, mask or other component. The second port may be operable to connect to another component, such as a flow restrictor, a filter, a ventilator circuit or other component. In some embodiments, the T-connector includes a valve configured to open during a user's inhalation and close during a user's exhalation. When closed, the valve may seal against a valve seat within the vertical tube. Some valve embodiments use a flexible membrane held by a connector around the center of the valve.

In some embodiments, the vertical tube includes an outer vertical port and an internal vertical port spaced within the outer vertical port and defining a gap. Some embodiments of the nebulizer's top are configured to fit in the gap. The outer vertical port includes one or more threads in some embodiments. The internal vertical port may be shorter than the outer vertical port and include a series of teeth at the distal end from the horizontal tube. In some embodiments, the teeth only extend around a portion of the distal end of the internal vertical port. In some embodiments, the internal vertical port's distal end is angular with some teeth extending further than other teeth from the horizontal port. In some embodiments, the teeth are configured to cut the internal seal and fold the seal downward to open the nebulizer for use.

In some embodiments, when the nebulizer is connected to the T-connector in a first position, the teeth do not engage the internal seal. In such embodiments, the T-connector is rotated during operation causing the teeth to engage and cut the internal seal. As the rotation continues, the seal is folded back between the nebulizer's top and the internal vertical port. In some embodiments, the seal may be configured to include ribs or elements configured to limit obstruction and airflow turbulence through the nebulizer output and vertical tube.

In some embodiments, the apparatus includes an internal seal when set in a first position and the internal seal operates as a valve when the apparatus is set in a second position. The nebulizer may include an output port with a flexible membrane at the top. The output port may be a tubular shape with the flexible membrane covering the top. In some embodiments, the output port's top surface operates as an element of a compression seal in a first position and a valve seat in a second position. An outer edge of the output port's top may not be covered by the flexible membrane in some embodiments.

The output port's outer surface may include one or more guide channels configured to connect with the T-connector. The guide channels may include one or more divots, concavities or other catch elements. In some embodiments, the catch elements may be associated with a first position of the apparatus and a second position of the apparatus.

The T-connector may include the horizontal tube and the vertical tube. In some embodiments, the vertical tube includes one or more protrusions on an interior surface. The protrusions may be longer at the top than the bottom creating an angled edge of the protrusion in some embodiments. The T-connector may also include an interior extension within the vertical port's interior surface. When connected to the nebulizer in a first position, the interior extension is an element of a compression seal with the flexible membrane between the interior extension and the nebulizer's output port. When the nebulizer is in a second position, the flexible membrane is free to operate as a one-way valve without interference from the interior extension.

In some embodiments, the T-connector attaches to the nebulizer's output port by pressing the T-connector onto the output port with the protrusions sliding into the guide channel. The T-connector may be pressed until the apparatus is in a first position with the flexible membrane trapped between the interior extension and the top of the nebulizer's output port. In some embodiments, the protrusions and catch element in the guide channel are configured to prevent the T-connector from being removed from the nebulizer.

In some embodiments, when the device is ready for use, the T-connector is rotated relative to the nebulizer to a second position. In the second position, the flexible membrane may be operable as a one way valve. In some embodiments, the protrusions and guide channels direct the rotation into the second position. The second position may cause the T-connector to move higher along the output port to create separation between the output port top and the interior extension.

Additional aspects, advantages and features are included in the following description of exemplary examples thereof, which description should be taken in conjunction with the accompanying figures, wherein like numerals are used to describe the same feature throughout the figures. All patents, patent applications, articles and other publications referenced herein are hereby incorporated herein in their entirety for all purposes.

A BRIEF DESCRIPTION OF THE DRAWINGS

Embodiments will now be described, by way of example only, with references to the accompanying drawings in which.

DETAILED DESCRIPTION

While this invention may be embodied in many different forms, there will herein be described in detail preferred embodiments of the invention with the understanding that the present disclosure is to be considered as an exemplification of the principles of the invention and is not intended to limit the broad aspects of the invention to the embodiments illustrated. It will be understood that the invention may be embodied in other specific forms without departing from the spirit or central characteristics thereof. The present embodiments, therefore, are to be considered in all respects as illustrative and not restrictive, and the invention is not to be limited to the details given herein.

The elements of the pre-filled, small-volume nebulizer and elements of the valve system are described further in the '907 application and '397 patent which may be referred to for further understanding of the present disclosure. These references also discuss benefits associated with a sealed, pre-filled, small-volume nebulizer (e.g. reducing contamination, operation steps, storage space, medicine dosage mistakes, etc.), a breath-actuated valve application (e.g. reducing medicine waste during exhalation, etc.) and additional physiotherapy associated with a flow restrictor in the T-connector.

Figure 1:
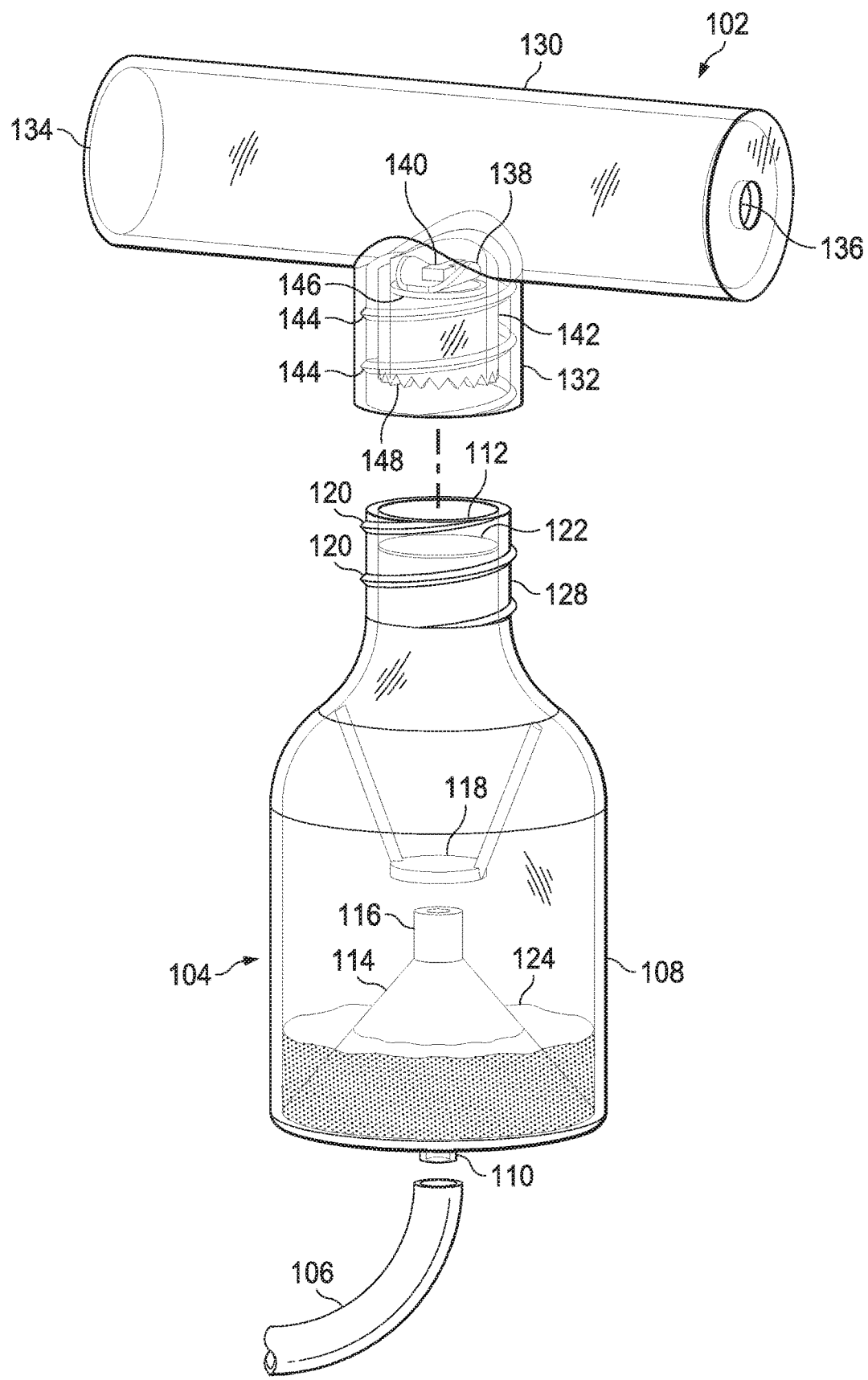
FIG. 1 is a side view of an embodiment of the apparatus depicting the T-connector separated from the nebulizer.
Figure 2:
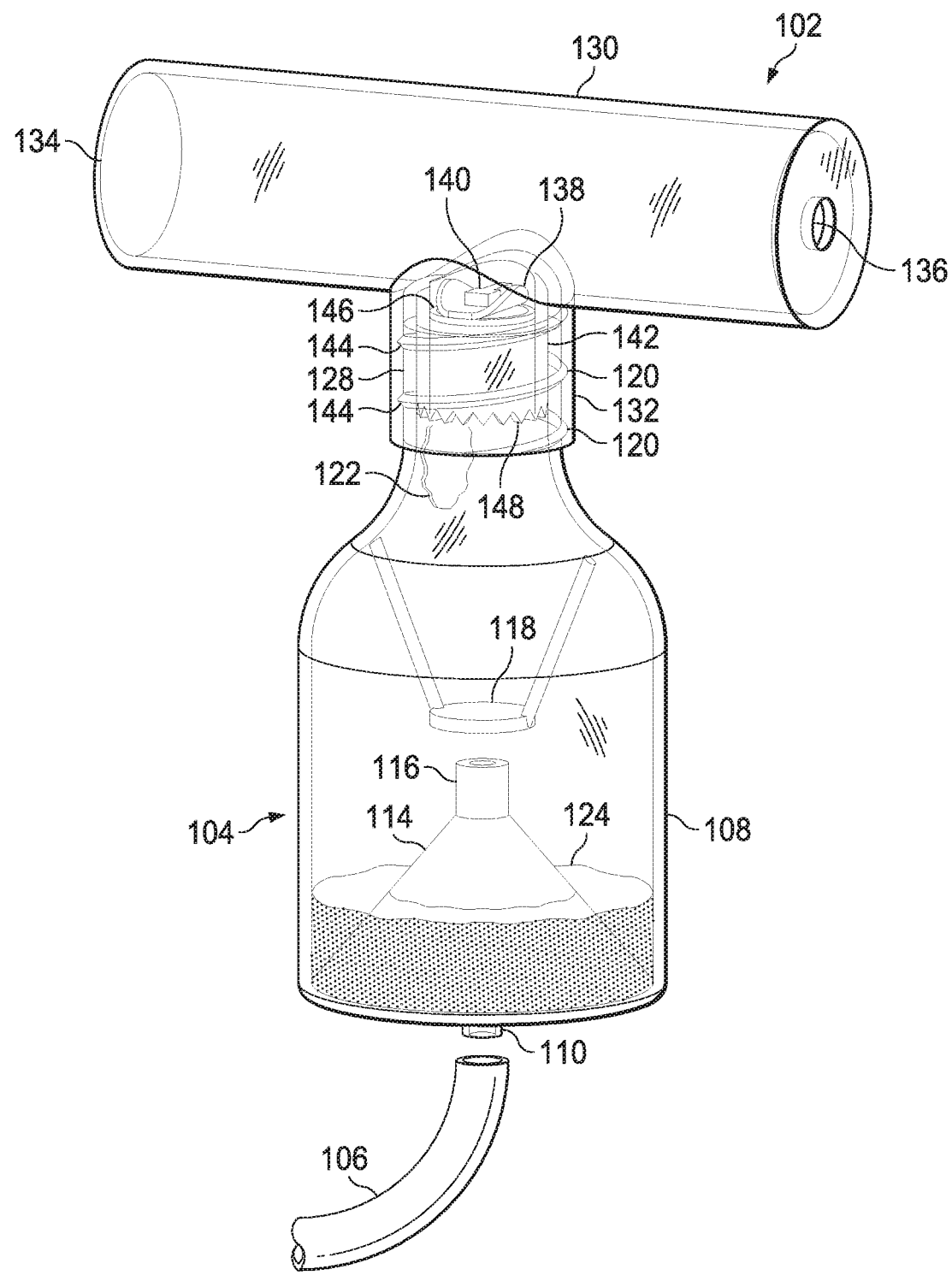
FIG. 2 is a side view of an embodiment of the apparatus depicting the T-connector attached to the nebulizer with the internal seal open.

FIGS. 1 and 2 illustrate an embodiment of a small volume nebulizer assembly, including a T-connector 102 and a small-volume nebulizer 104. Components may be fabricated via injection molding of a plastic compound, such as polypropylene or other plastic compound with appropriate properties for housing medication and fabricating a nebulizer. The small-volume nebulizer 104 may be comprised of a housing or body 108 containing a pre-filled unit-dose of medication 124, a siphon 114, a jet 116, a baffle 118, an output port 128 with an opening 112 and an input port 110 that connects to a gas source tube 106 (as shown in FIG. 2). In some embodiments, the housing 108 may comprise a housing top and a housing bottom connected at a housing seal.

The input port 110 includes a sealing component to prevent medicine from leaking out of the housing 108. The sealing component may be a check valve, a cap, a pierceable seal or other component. In some embodiments, the sealing component is removed prior to attaching the gas source tube 106 to the input port 110. In some embodiments, the sealing component is configured to open when the gas source tube 106 is attached or during the nebulizer's 104 operation. In some embodiments, the input sealing component may be an internal seal with components configured to operate as discussed further regarding the nebulizer's 104 output port 128.

The output port 128 includes an opening 112 at the top, external threads 120 and an internal seal 122. The internal seal 122 prevents medicine from leaking out of the housing 108 from the output port 128. In this embodiment, the internal seal 122 and the input port's 110 sealing component collectively seal the housing 108 to prevent loss of medicine and reduce the likelihood of contamination.

The T-connector 102 includes a horizontal tube 130 with two ends. The front port 134 is configured to provide a patient interface. In some embodiments, the front port 134 may comprise a mouthpiece. In other embodiments, the front port 134 may be connectable to a mouthpiece, mask or other patient interface component. On the opposite end of the horizontal tube 130 is a flow restrictor 136. In this embodiment, the flow restrictor 136 allows ingress and egress of ambient air and facilitates physiotherapy. In other embodiments, the second end of the horizontal tube 130 may have a port for connection to other components. For example, the horizontal tube 130 may be connected in-line with a ventilator circuit.

In this embodiment, a vertical tube 132 is located between the two ends of the horizontal tube 130. Within the vertical tube 132 is an interior tube 142 that is vertically shorter than the outer vertical tube 132. A valve comprising a center pivot 140 holding a valve gate 138 in place. The valve gate 138 is made of an appropriate substance, such as neoprene, which has the qualities of being lightweight, flexible, and impervious to liquid. Valve gate 138 is in a normally closed position until forced open by a drop in pressure within horizontal tube 130 corresponding to a user's inspiration. During expiration, the valve gate 138 returns to a closed position creating a seal against the valve seat 146. The valve seat 146 is a ring extending within the inner wall of the interior tube 142.

In this embodiment, the bottom edge of the interior tube 142 includes teeth 148. The teeth 148 may extend around all of the bottom edge or only a portion of the bottom edge in some embodiments. In some embodiments, the teeth 148 may extend different vertical lengths allowing a portion of the teeth 148 to contact the internal seal 122 prior to other teeth 148. In some embodiments, the teeth 148 are aligned on an angle that extends from a first point 360 degrees until reaching the first point again with the start a first vertical distance and the stop a second vertical distance.

The outer vertical tube 132 also includes threads 144 (shown by notches on the sides) on the interior wall. The threads 144 in the vertical tube 132 correspond with the threads 120 on the exterior of the output port 128 facilitating a connection between the T-connector 102 and the nebulizer 104. The spacing of the threads 120 and 144, the internal seal 122 and the bottom of the interior tube 142 is configured to allow the nebulizer assembly to be connected in a first position with the internal seal 122 intact and move to a second position wherein the interior tube's 142 teeth 148 have opened the internal seal 122 as illustrated in FIG. 2.

In this embodiment, the T-connector 102 rotates relative to the nebulizer 104 with the threaded connection between threads 120 and 144. As the T-connector 102 rotates, the teeth 148 engage the internal seal 122 and cut a portion of the internal seal 122. Once a portion of the internal seal 122 is cut, the seal 122 folds between the interior wall of the output port 128 and the exterior wall of the interior tube 142. In some embodiments, the internal seal 122 may include ribs or other structural features configured to cause the internal seal 122 to form against the interior wall of the output port 128 limiting airflow interference or turbulence caused by the seal 122.

During manufacture, the nebulizer 104 may be sterilized, pre-filled with a unit dose of medication 124 and sealed with an input port sealing component and the internal seal 122. The T-connector 102 may also be sterilized. The T-connector 102 is attached to the nebulizer's 104 output port 128 and the assembly is connected in a first position. In some embodiments, a medication label may be affixed to the assembly indicating the medicine and dosage, as well as other usage and medication information. In some embodiments, the medication label, other label or element may be placed over the connection between the T-connector 102 and the nebulizer 104 to indicate that the assembly is in the first position and the internal seal 122 has not been broken.

The assembly may be packaged, transported and stored in the first position maintaining the pre-filled, sealed nebulizer 104. When the assembly is ready for use, the gas source tube 106 is connected to the input port 110. The T-connector 102 is rotated relative to the nebulizer 104 causing the internal seal 122 to open. During operation, high-pressure gas is introduced into the input port 110 from gas source tube 106 which is connected prior to use. Gas flows into the input port 110 at an appropriate flow rate, typically ranging from 6 to 10 liters per minute, and is directed through jet 116, which has a narrowed orifice in order to accelerate the velocity of the gas. One skilled in the art will recognize that the gas will typically be oxygen, air and/or another gas and remain within the scope and spirit of the disclosure. In some embodiments, the gas will be provided by a compressed gas source. As the velocity increases, pressure within siphon 114 drops creating a suction, which serves to entrain medication 124. Medication 124 is hurled as spray against baffle 118. Baffle 118 is a surface that causes large particles to fall out of suspension, thus reducing the overall average particle size of the aerosol. After the sprayed medication encounters the baffle 118, the remaining particles are suspended within the nebulizer's 104 housing 108 until valve gate 138, located within output port 128 and stabilized by valve gate center pivot 140, opens in order to allow egress of the aerosol particles from nebulizer's 104 housing 108 and into horizontal tube 130.

FIGS. 3-7 show another nebulizer assembly embodiment. The nebulizer assembly includes a T-connector 200 and a nebulizer 204. The nebulizer 204 is shown cut off with only the output port 218 illustrated. Other than the elements discussed for the output port 218, the nebulizer 204 may be any pre-filled, small-volume nebulizer—such as nebulizer 104 described above or the nebulizers described in the '907 application and '397 patent.

Figure 3:
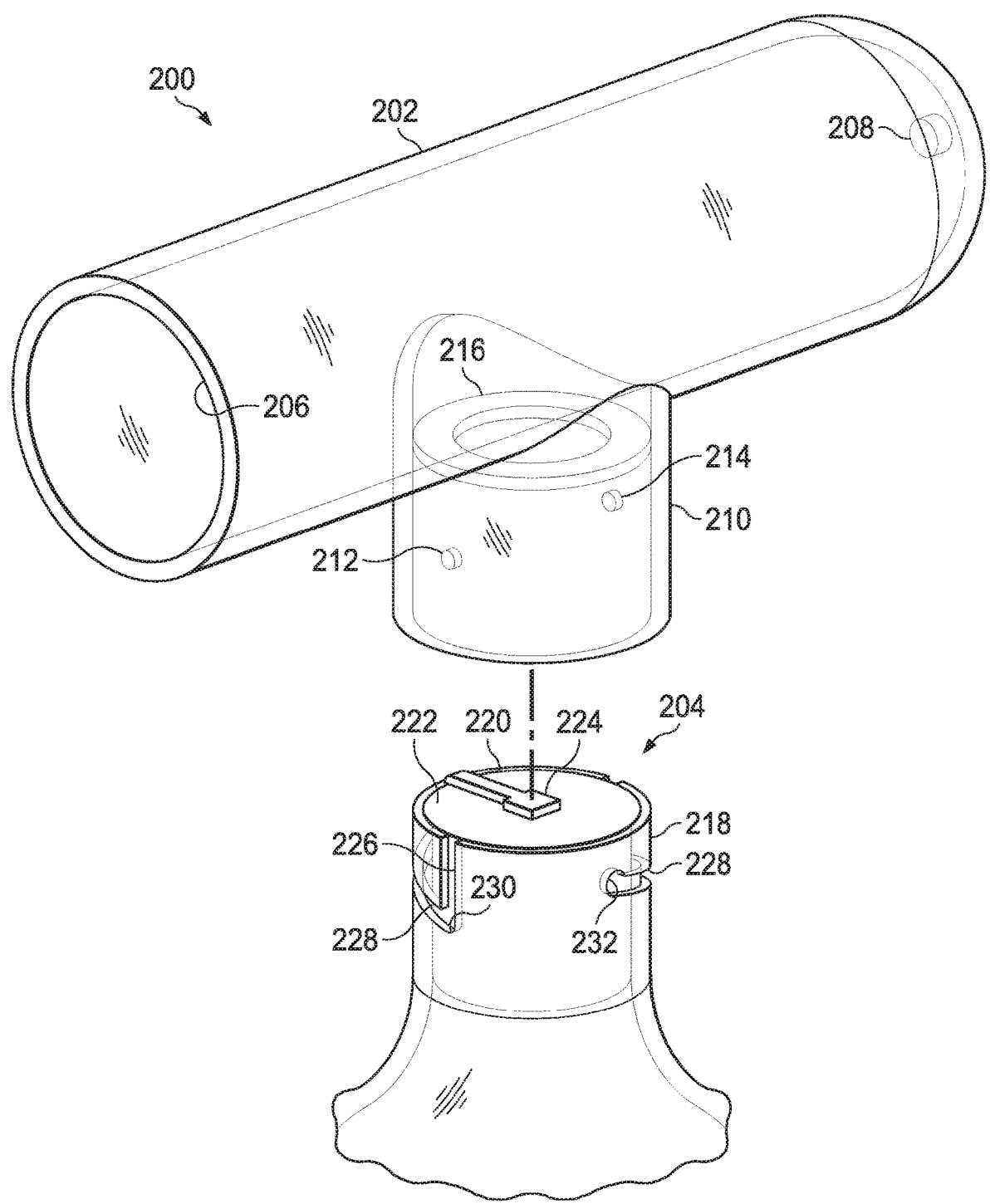
FIG. 3 is a side view of another embodiment of the apparatus depicting the T-connector separated from the nebulizer.
Figure 4:
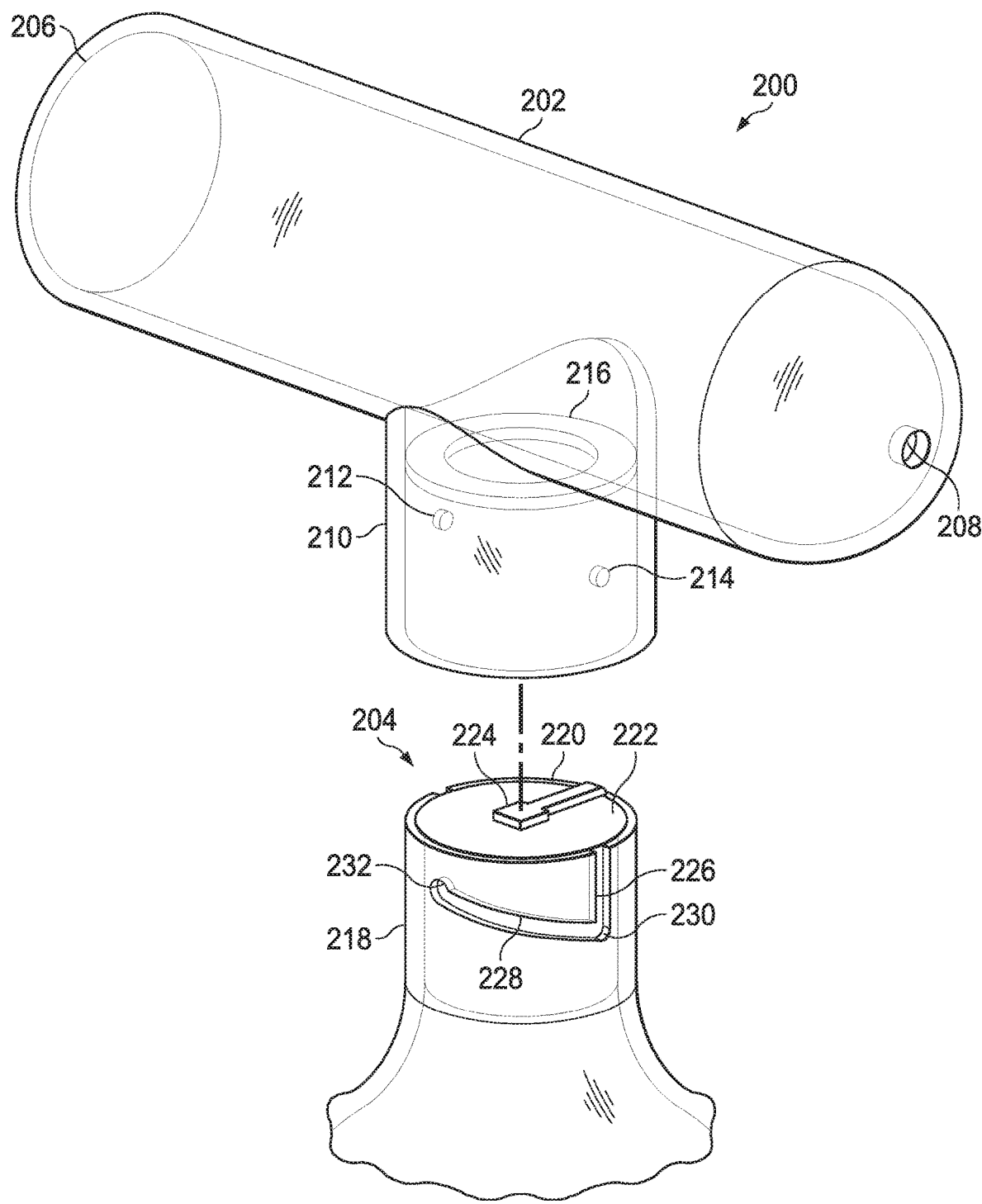
FIG. 4 is a back view of the embodiment of the apparatus in FIG. 3 depicting the T-connector separated from the nebulizer.

FIGS. 3 and 4 show the assembly components from a side view and a back view respectively. The T-connector 200 includes a horizontal tube 202 with a patient interface port 206 and a flow restrictor 208. As discussed above, aspects of the horizontal tube 202—such as the end configurations—may vary and remain within the scope and spirit of the disclosure. The T-connector 200 also includes a vertical tube 210 between the patient interface port 206 and the flow restrictor 208.

In this embodiment, a first protrusion 212 and a second protrusion 214 are located on an interior surface of the vertical tube 210 near the bottom. The protrusions 212 and 214 may have an angled surface with the bottom length shorter than the upper length. In some embodiments, the protrusions 212 and 214 may be rounded. In some embodiments, the number and design of the protrusions 212 and 214 may vary. In addition, an internal extension ring 216 extends around the interior surface of the vertical tube 210 near the top of the vertical tube 210.

Figure 5:
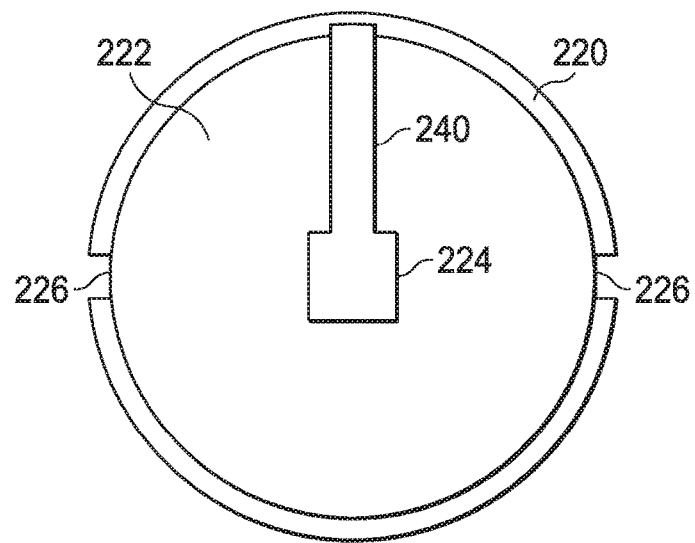
FIG. 5 is a top view of the embodiment of the nebulizer from FIG. 3.
Figure 6:
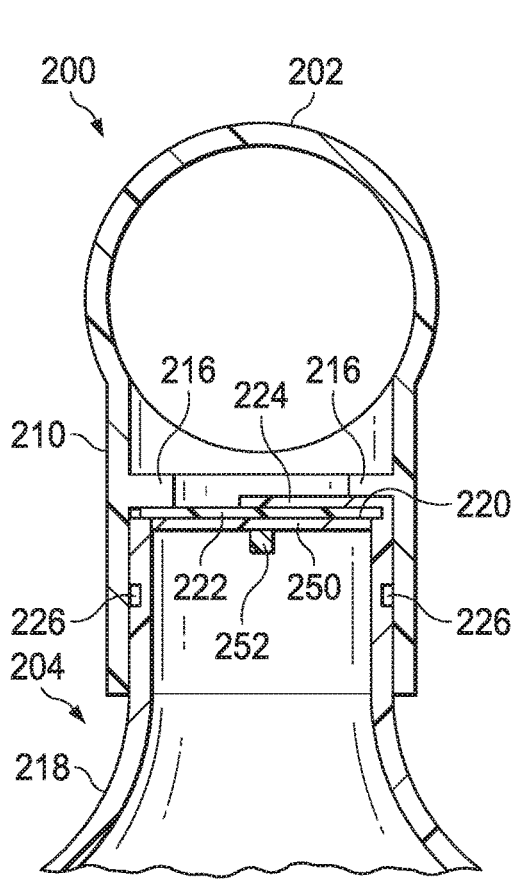
FIG. 6 is a cross-section view of the embodiment of the apparatus form FIG. 3 from the front depicting the T-connector attached to the nebulizer in a first position.
Figure 7:
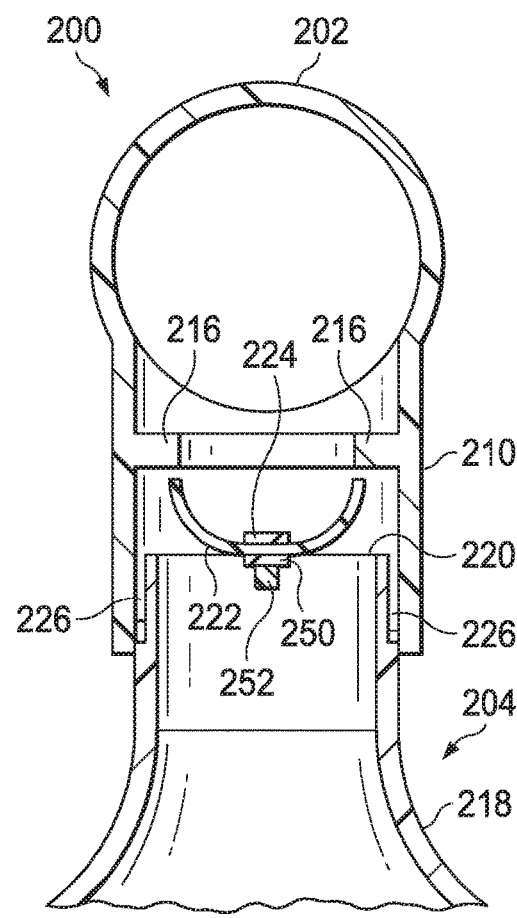
FIG. 7 is a cross-section view of the embodiment of the apparatus form FIG. 3 from the front depicting the T-connector attached to the nebulizer in a second position.

The nebulizer's 204 output port 218 includes a top surface 220 that operates as a valve seat for a valve gate 222. The valve gate 222 is held in place by center pivot 224. As shown in FIG. 5, the center pivot 224 connects to the top surface 220 by arm 240. In some embodiments, the center pivot 224 may be a separate component. As shown in FIGS. 6 and 7, the center pivot 224 includes a tab 252 configured to pass through the valve gate 222 and a mount structure 250 to hold the valve gate 222 in place against the mount structure 250. The mount structure 250 may be a strut or other element extending across the top of the output port from one interior surface of the output port 218 to the opposite interior surface.

The outside surface of the output port 218 includes a pair of guide channels corresponding to the protrusions 212 and 214. The guide channels include a first channel section 226 that extends vertically from the top of the output port 218 to a first catch element 230—e.g. a divot, a concavity, etc. In some embodiments, the catch element 230 may include an area defined by a rib or shelf on the upper side of the area configured to prevent removing the T-connector 200 vertically from the nebulizer 204. The guide channel also includes a second channel section 228 at an upward angle from the first catch element 230 to a second catch element 232.

When the protrusions 212 and 214 are located in the first catch element 230, the assembly is in a first position. A cross-section of the assembly in the first position is shown in FIG. 6. In this position, the valve gate 222 is between the top surface 220 of the output port 218 and the extension ring 216 of the T-connector 200. In this position, the valve gate 222 is held in a closed position and operates as an internal seal preventing ingress or egress from the nebulizer's 204 output port 218. In some embodiments, a gasket or other sealing component may be on the bottom of the extension ring 216. In some embodiments, the valve gate 222 is compressed between the extension ring 216 and the top surface 220.

In some embodiments, the protrusions 212 and 214 and guide channel elements may be configured to prevent tampering and reuse of the assembly, preventing misuse and contamination associated with repetitive use of the nebulizer assembly.

When the assembly is ready for use, the T-connector 200 is rotated relative to the nebulizer 204 with the protrusions 212 and 214 moving along the second channel sections 228 of guide channels. As the T-connector 200 rotates, the distance between the extension ring 216 and the top surface 220 increases consistent with the upward angle of the second channel section 228.

When the protrusions 212 and 214 are located in the second catch element 232, the assembly is in a second position. A cross-section of the assembly in the second position is shown in FIG. 7. In this position, the valve gate 222 is on the top surface 220 of the output port 218 and separated from the extension ring 216 of the T-connector 200. In this position, the valve gate 222 is free to open and close in conjunction with a user's inhalation and exhalation.

This assembly allows the valve gate 222 to operate as an internal seal when the components are in one configuration and a valve when the components are in a second configuration.

During manufacture, the nebulizer 204 may be sterilized, pre-filled with a unit dose of medication and sealed. The T-connector 200 may also be sterilized. The T-connector 200 is attached to the nebulizer's 204 output port 218 and the assembly is connected in a first position. In some embodiments, a medication label may be affixed to the assembly indicating the medicine and dosage, as well as other usage and medication information. In some embodiments, the medication label, other label or element may be placed over the connection between the T-connector 200 and the nebulizer 204 to indicate that the assembly is in the first position and the internal seal—created by valve gate 222 held in place between the extension ring 216 and top surface 220—has not been opened.

The assembly may be packaged, transported and stored in the first position maintaining the pre-filled, sealed nebulizer 204. When the assembly is ready for use, a gas source tube is connected to the input port of the nebulizer 204. The T-connector 200 is rotated relative to the nebulizer 204 causing the distance between the top surface 220 and the extension ring 216 to increase allowing the valve gate 222 to operate as a breath-actuated nebulizer valve.

During operation, medicine is aerosolized in the nebulizer's 204 housing and is suspended within the nebulizer's 204 housing until valve gate 222 opens in order to allow egress of the aerosol particles from nebulizer 204 and into horizontal tube 202.

In some embodiments, the configuration of components may be inverted with the nebulizer's 204 output port 218 on the outside of the T-connector's 200 vertical tube 210. In such an embodiment, a valve seat, mount structure 250, center pivot 224 and valve gate 222 may be recessed within the output port 218. The bottom edge surface of the vertical tube 210 may act as the second element holding the valve gate 222 against the valve seat within the output port 218.

In some embodiments, alternative connection mechanisms may be used in place of or in conjunction with the threads or protrusions and guide channel systems disclosed.

In some embodiments, the internal valve and seal configuration may be used in other applications. The internal valve and seal configuration may be in a tube system and operable to seal the tube in both directions in one configuration and to operate as a one-way valve in a second configuration.

Figure 8:
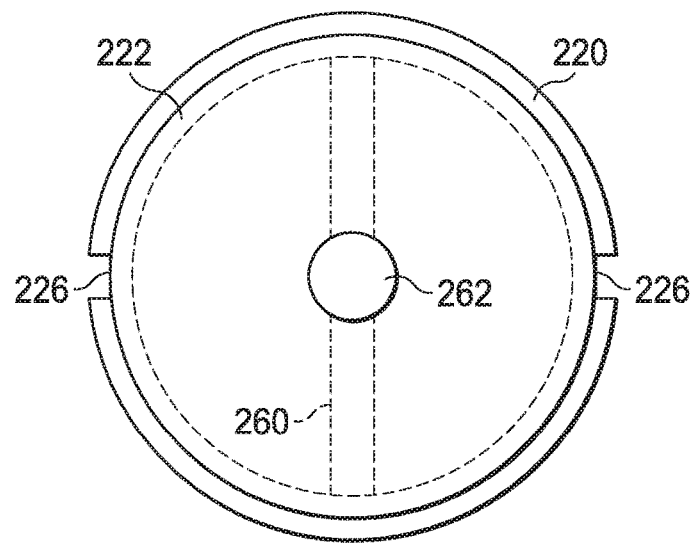
FIG. 8 is a top view of another embodiment of a nebulizer.
Figure 9:
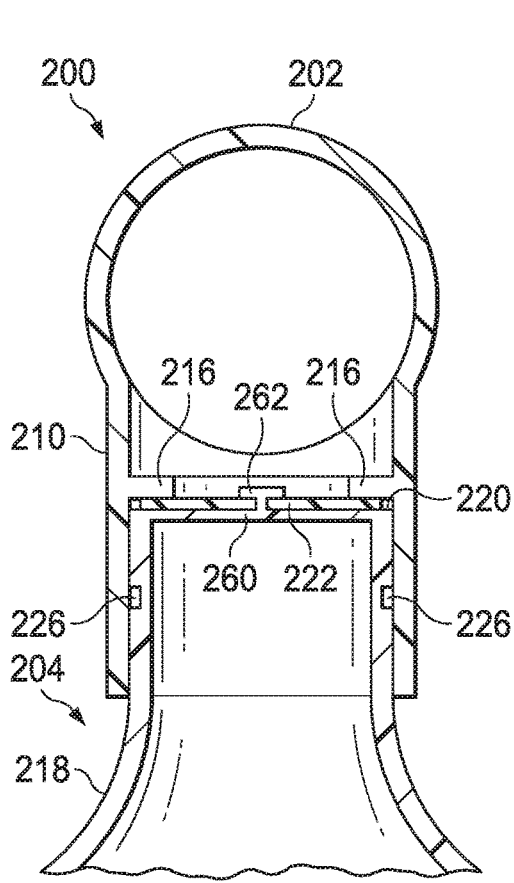
FIG. 9 is a cross-section view of an embodiment of the apparatus from the front depicting the T-connector attached to the nebulizer of FIG. 8 in a first position.
Figure 10:
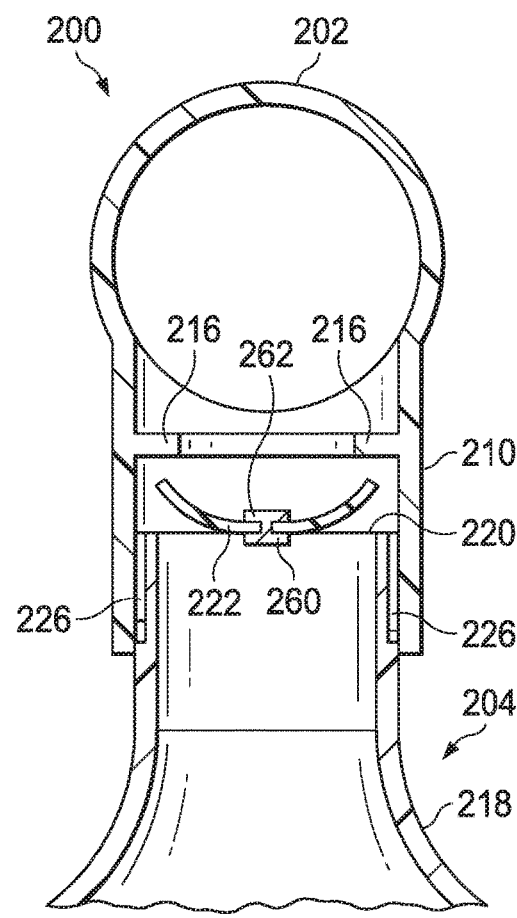
FIG. 10 is a cross-section view of the embodiment of the apparatus form FIG. 9 from the front depicting the T-connector attached to the nebulizer in a second position.

FIGS. 8-10 show another nebulizer assembly embodiment similar to the assembly shown in FIGS. 3-7. The nebulizer assembly includes a T-connector 200 and a nebulizer 204. Other than the elements discussed for the valve seat configuration below, this embodiment operates the same as the embodiment discussed with FIGS. 3-7 above.

As discussed above, the nebulizer's 204 output port 218 includes a top surface 220 that operates as a valve seat for a valve gate 222. In this embodiment, the valve gate 222 is held in place by center pivot 262 which is connected to mount structure 260. As shown in FIG. 8, the mount structure 260 is below the valve gate 222. The mount structure 260 may be a strut or other element extending across the top of the output port 218 from one interior surface of the output port 218 to the opposite interior surface. As shown in FIGS. 9 and 10, the center pivot 262 passes through the valve gate 222 to the mount structure 260 and holds the valve gate 222 in place against the mount structure 260. The center pivot 262 may be formed as part of the mount structure 260 or as a separate element that connects to the mount structure 260. If the cinter pivot 262 is formed with the mount structure 260, the valve gate 222 may include a resilient center opening that may be expanded to fit over the top of center pivot 262 and return to a smaller default size fitted between the upper portion of center pivot 262 and the mount structure 260.

When the protrusions 212 and 214 are located in the first catch element 230, the assembly is in a first position. A cross-section of the assembly in the first position is shown in FIG. 9. In this position, the valve gate 222 is between the top surface 220 of the output port 218 and the extension ring 216 of the T-connector 200. In this position, the valve gate 222 is held in a closed position and operates as an internal seal preventing ingress or egress from the nebulizer's 204 output port 218. In some embodiments, a gasket or other sealing component may be on the bottom of the extension ring 216. In some embodiments, the valve gate 222 is compressed between the extension ring 216 and the top surface 220.

When the assembly is ready for use, the T-connector 200 is rotated relative to the nebulizer 204 with the protrusions 212 and 214 moving along the second channel sections 228 of guide channels. As the T-connector 200 rotates, the distance between the extension ring 216 and the top surface 220 increases consistent with the upward angle of the second channel section 228.

When the protrusions 212 and 214 are located in the second catch element 232, the assembly is in a second position. A cross-section of the assembly in the second position is shown in FIG. 10. In this position, the valve gate 222 is on the top surface 220 of the output port 218 and separated from the extension ring 216 of the T-connector 200. In this position, the valve gate 222 is free to open and close in conjunction with a user's inhalation and exhalation.

This assembly allows the valve gate 222 to operate as an internal seal when the components are in one configuration and a valve when the components are in a second configuration.

In some embodiments, alternative connection mechanisms may be used in place of or in conjunction with the threads or protrusions and guide channel systems disclosed.

In some embodiments, the internal valve and seal configuration may be used in other applications. The internal valve and seal configuration may be in a tube system and operable to seal the tube in both directions in one configuration and to operate as a one-way valve in a second configuration.

The invention being thus described and further described in the claims, it will be obvious that the same may be varied in many ways. Such variations are not to be regarded as a departure from the spirit and scope of the invention and all such modifications as would be obvious to one skilled in the art are intended to be included within the scope of the apparatuses and methods described.

The invention claimed is:

1. A pre-filled, small-volume nebulizer assembly comprising:
   a small-volume nebulizer body comprising:
      an aerosolizing chamber having an output port on top and a seal in the output port, wherein contained within said aerosolizing chamber is a siphon, a jet, a baffle and a unit-dose of medication, wherein said output port includes a first connector component on an exterior surface;
   a T-connector attached to the output port, wherein the T-connector includes a patient interface tube at a top of a vertical tube, wherein the patient interface tube includes a patient opening and a secondary opening, and wherein the vertical tube includes a valve proximate to the top of the vertical tube, an interior surface having a second connector component to correspond with said first connector component, and an interior tube within the vertical tube below the valve, wherein said interior tube is shorter than the vertical tube and includes a series of teeth at a bottom edge of said interior tube;
   wherein said small-volume nebulizer assembly has a first configuration and a second configuration, and said T-connector is rotatable relative to said small-volume nebulizer body to change said small-volume nebulizer assembly from said first configuration to said second configuration,
      in said first configuration, said seal prevents said unit-dose of medication from exiting said small-volume nebulizer body, and
      during said change from said first configuration to said second configuration, said teeth cause the seal to open, and
      in said second configuration, when said seal is open, airflow from said small-volume nebulizer body is able to pass into said interior tube, wherein, during operation of the small-volume nebulizer assembly by a user, the valve opens with an inhalation by the user and closes with an exhalation by the user.

2. The small-volume nebulizer assembly of claim 1, wherein said secondary opening is a flow restrictor.

3. The small-volume nebulizer assembly of claim 1, wherein said valve includes a valve gate that is a flexible membrane.

4. The small-volume nebulizer assembly of claim 1, wherein said valve includes a valve gate that is attached to a mount structure by a center pivot.

* * * * *